(12) United States Patent
Fawzy (10) Patent No.: US 10,215,632 B2
(45) Date of Patent: Feb. 26, 2019

(54) METHOD AND APPARATUS FOR SPECTRAL REFLECTANCE IMAGING USING DIGITAL CAMERAS

(71) Applicant: Zycor Labs Inc., Richmond (CA)

(72) Inventor: Yasser Fawzy, Vancouver (CA)

(73) Assignee: Zycor Labs Inc., Richmond (CA)

( * ) Notice: Subject to any disclaimer, the term of this patent is extended or adjusted under 35 U.S.C. 154(b) by 0 days.

(21) Appl. No.: 15/703,981

(22) Filed: Sep. 13, 2017

(65) Prior Publication Data
US 2018/0188108 A1 Jul. 5, 2018

Related U.S. Application Data

(60) Provisional application No. 62/396,730, filed on Sep. 19, 2016.

(51) Int. Cl.
| | |
|---|---|
| *G01J 3/46* | (2006.01) |
| *G01J 3/02* | (2006.01) |
| *G01J 3/42* | (2006.01) |
| *G01J 3/50* | (2006.01) |
| *G01J 3/10* | (2006.01) |

(Continued)

(52) U.S. Cl.
CPC ............ *G01J 3/027* (2013.01); *A61B 5/0075* (2013.01); *A61B 5/444* (2013.01); *G01J 3/02* (2013.01); *G01J 3/0232* (2013.01); *G01J 3/10* (2013.01); *G01J 3/2823* (2013.01); *G01J 3/42* (2013.01); *G01J 3/50* (2013.01); *G01J 2003/102* (2013.01)

(58) Field of Classification Search
CPC ........ G01J 3/46; G01J 3/50; G01J 3/02; G01J 3/524; G01J 3/51
USPC ........................................................ 356/402
See application file for complete search history.

(56) References Cited

U.S. PATENT DOCUMENTS 7,567,293 B2 7/2009 Perlman et al.
2005/0225501 A1* 10/2005 Srinivasan ........... G02B 3/0031
345/32

(Continued)

FOREIGN PATENT DOCUMENTS

CN 104545815 A1 4/2015

*Primary Examiner* — Md M Rahman
(74) *Attorney, Agent, or Firm* — Oyen Wiggs Green & Mutala LLP (57) ABSTRACT

A method and spectral light-based apparatus with an embedded (built-in) spectral calibration module for acquiring multi-spectral reflectance images from a digital camera are disclosed. The apparatus may be an attachment device, which may be integrated with a consumer digital camera (such as smartphone camera), and may measure and/or estimate spectral reflectance and true color values for an object recorded by the camera. An example apparatus comprises an array of monochromatic light sources, preferably pulsed LEDs, irradiating in a time-multiplexed manner to generate light spectra in the range of 400 nm-1000 nm, an optical lens to limit the field of view of the attached camera, an electro-mechanical shutter or plate with its inner (reflection) surface coated with a diffuse reflectance standard to ensure flat spectral response, and an interface module for synchronizing the time-multiplexed light spectra with the coated shutter opening and closing and with the digital frames acquired by the camera, such that the true spectral reflectance and true color value of an object can be measured.

9 Claims, 10 Drawing Sheets

(51) Int. Cl.
 *G01J 3/28* (2006.01)
 *A61B 5/00* (2006.01)

(56) References Cited

U.S. PATENT DOCUMENTS

2010/0182496 A1* 7/2010 Brady .................... G02B 26/02
 348/362
2011/0280561 A1 11/2011 Geffert et al.
2013/0308045 A1 11/2013 Rhoads et al.
2016/0262605 A1 9/2016 Taylor et al.
2016/0291326 A1* 10/2016 Evans ................ G02B 27/0172

* cited by examiner

METHOD AND APPARATUS FOR SPECTRAL REFLECTANCE IMAGING USING DIGITAL CAMERAS

CROSS-REFERENCE TO RELATED APPLICATIONS

This application claims the benefit under 35 U.S.C. § 119 of US Application No. 62/396730 filed 19 Sep. 2016 and entitled METHOD AND APPARATUS FOR SPECTRAL REFLECTANCE IMAGING USING DIGITAL CAMERAS which is hereby incorporated herein by reference for all purposes.

FIELD

This invention relates to imaging. Some embodiments provide spectral intensity calibration devices for cameras. Such devices may be provided as camera accessories or may be built into cameras. Applications of the invention include multi-spectral imaging. Some embodiments provide camera-based devices configured for multi-spectral imaging and color shade measurements.

BACKGROUND

Spectral reflectivity is the fraction of light reflected by an object. This fraction typically varies with the wavelength of light incident on the object. Spectral reflectivity can be used to characterize the surface of an object. Digital cameras can be used to estimate the spectral reflectance of a surface. However, digital cameras are not optimized for measuring spectral reflectance or for quantitative color measurements.

Most digital cameras capture digital color images in a trichromatic fashion using three distinct sets of detectors. The detectors may, for example, be complementary metal-oxide semiconductor ("CMOS") or charge-coupled device ("CCD") sensors. Each set of detectors is sensitive to different wavelengths (colors) of light. Typical digital cameras have detectors sensitive to each of: red (R), green (G), and blue (B) light. Such cameras ("RGB digital cameras") are incapable of reproducing hi-fidelity color images which are required in fields such as tele-dermatology. In addition, RGB digital cameras have a limited color gamut and cannot reproduce a full range of colors and shades. These inherent limitations are more pronounced when the surface of an object contains reddish colors.

Because of the limitations of RGB digital cameras, RGB digital cameras cannot be used where accurate measurement and/or reproduction of colors is required. For example, RGB digital cameras have limited application in color reproduction for tele-medicine, image archiving and follow-up, color matching and measurements, and tissue characterization and quantification in cancer characterization.

One method for obtaining accurate information about the color of a surface using a RGB digital camera is to use the camera to obtain images while illuminating the surface with spectral light at different wavelengths. The spectral light comprises a set of spectral bands, preferably narrow bands, centered on each of the different wavelengths. The spectral reflectance images are then acquired using an RGB camera. If the sensitivity of the sensors of the RGB camera at the wavelengths of the spectral light are known and the intensity of illumination in the different bands of the spectral light are known then the resulting set of images can be processed to determine the spectral reflectance of the surface.

This method is cost effective but requires a spectrometer and a dedicated lab facility to characterize the spectral sensitivity of digital camera sensors. It further requires pre-measurement calibration using a calibration target with a known reflectance at each wavelength, e.g. a white 99% diffuse reflectance disk. The pre-measurement calibration using a white diffuse reflectance disk ensures the effective spectral calibration of a camera sensor, especially when used to acquire spectral images in a non-lab-controlled environment.

There remains a need for digital cameras which can provide accurate spectral images of a target, even in dynamically changing viewing or illumination conditions. There is a particular need for such cameras that are cost effective enough for widespread application in fields such as tele-dermatology, color matching and the like.

SUMMARY

This invention has a number of aspects. These aspects may be combined but may also be applied individually or in sub-combinations. These aspects include, without limitation:
  multi-spectral imaging attachments for use with digital cameras. Such attachments may include light sources and calibration devices;
  digital cameras with built-in multi-spectral imaging capabilities;
  calibration devices for use with digital cameras, such devices may include reflective surfaces that can be selectively placed in the field of view of the camera. Such calibration devices may be applied to determine intensities of different bands of spectral light for multi-spectral imaging or to characterize ambient light;
  software (which may be in the form of firmware or and app, for example) useful for performing multi-spectral imaging using a digital camera;
  methods for calibrating digital cameras; and
  methods for acquiring multi-spectral images using digital cameras.

One example aspect provides a fully portable apparatus that can be integrated with or attached to a consumer/commercial digital camera to provide a spectral imaging and color value measurement device.

One aspect of the invention provides a spectral light source having an embedded (built-in) spectral intensity calibration module combined with a digital camera-based device, for use in multi-spectral imaging and/or true color shade measurements. The spectral light source and calibration module may be provided as an accessory or add-on to the digital camera or may be built in to the digital camera. The digital camera may be a purpose-built camera or a camera that forms part of a computing device such as a camera of a smartphone or tablet or an accessory camera attached to a personal computer, for example.

Another aspect of the invention provides cameras equipped with shutters having surfaces that have a known, preferably flat spectral response. The shutters, may, for example, be coated with a white or grey surface coating. Such shutters may be used to calibrate the cameras. Such shutters may be built into a camera or added as an accessory. Some embodiments include a control unit that processes images of the shutter illuminated by ambient light to characterize the ambient light or images of the shutter illuminated by spectral light to characterize the spectral light.

Another aspect of the invention provides a multi-spectral imaging system. The multi-spectral imaging system comprises a digital camera having an imaging lens. A spectral intensity calibration module includes an electro-mechanical shutter coated with a material having a known reflectance (e.g. a white or grey coating) and a control module. A spectral light source is arranged to illuminate an object in a field of view of the lens or the surface of the electromechanical shutter depending on whether the shutter is open or closed. The control module synchronizes electrical triggering of the light source with opening or closing of the shutter.

Another aspect of the invention provides a multi-spectral imaging system. The multi-spectral imaging system comprises a digital camera having an imaging lens; a spectral light source; and a control module. The control module synchronizes electrical triggering of the light source to emit bands of one or more different wavelengths with acquisition of an image by the camera.

An example spectral light apparatus accessory comprises a housing which encloses a spectral light source operative to produce different monochromatic wavelengths; an optical lens system aligned with an optical axis of a camera such as a smartphone camera; and an electro-mechanical shutter (such as a leaf camera shutter) covering a distal opening in the housing. The spectral light source may be controlled to emit different wavelengths in a time-multiplexed manner. The housing limits the field of view of the camera to the area defined by the distal opening in the housing. The shutter can selectively cover or leave open the distal opening of the housing. A surface of the shutter facing the camera is coated with a standard diffuse reflectance coating to produce a known, preferably flat, spectral response suitable for spectral calibration. The optical lens system controls the optical coupling of a lens of the smartphone camera to ensure that it captures only the reflected light originating from the interaction of the spectral light with the object or surface being imaged. The housing comprises a built-in and time-synchronized spectral calibration module, which performs spectral calibration under the same viewing conditions as the acquired spectral images of the object or surface being imaged.

The spectral light source may comprise an array of light-emitting diodes ("LEDs"). Control circuits may electrically synchronize operation of the LEDs with the smartphone or digital camera trigger control, and the opening or closing of the white reflectance-coated mechanical shutter. Analysis software such as a function built into firmware of the camera or a mobile app uses the acquired synchronized frames to calculate the spectral reflectance of the object or surface that is illuminated by the light source. The analysis software uses the acquired frames obtained from the embedded coated shutter when it is closed, and uses the frames obtained from the object or surface when the shutter is opened, in order to estimate spectral reflectance and/or color values of the object or surface being imaged.

Another aspect of the invention provides a spectral light apparatus that can be used with a digital camera, such as a smartphone camera. This apparatus allows a digital camera to acquire spectral reflectance images and color values from an object or surface.

Another aspect of the invention provides methods for multi-spectral imaging.

A further aspect of the present invention provides a digital camera suitable for skin imaging, and in particular for generating depth-resolved skin images from acquired spectral images.

Various embodiments of the present invention have medical and/or non-medical applications, including performing tele-medicine procedures (such as tele-dermatology), performing color matching, improving color image synthesis and realism, performing computer-aided diagnosis ("CAD"), and quantifying and characterizing tissue/material properties and changes.

Further aspects and example embodiments are illustrated in the accompanying drawings and/or described in the following description.

BRIEF DESCRIPTION OF THE DRAWINGS

The accompanying drawings illustrate non-limiting example embodiments of the invention.

DETAILED DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive sense.

One embodiment of the present invention relates to a digital camera-based device having a built-in spectral intensity calibration module. This device may be attached to any digital camera including, for example, a smartphone camera. The device allows the digital camera to perform multi-spectral imaging and/or color shade measurement. The device may dynamically re-calibrate the digital camera when viewing or illuminations conditions change.

The general principles of spectral imaging using a calibration surface when producing images will now be described, followed by a description of some specific example embodiments of the invention.

A digital camera system equipped to perform multi-spectral imaging may apply the following principle. The measured signal reflected from some target (TARGT) and recorded by the digital camera system can be described by the following model:

$$I_{TARGT}(t,x,y)=\int F(\lambda)E(\lambda)S(\lambda)R(\lambda)d\lambda,$$

where $\lambda$ is the wavelength of illumination, $I_{TARGT}$ is the measured spectral reflectance of the target at a certain location and point in time, $F(\lambda)$ is the response of the optical system (including the response of the optical lens and/or filters), $E(\lambda)$ is the spectrum of the light source, $S(\lambda)$ is the camera sensitivity, and $R(\lambda)$ is the target's real reflectance spectrum.

A sequentially flashed light (such as the light emitted by a pulsed LED ring), illuminating both a target and a calibration surface at the same distance as the target, may be described by the following model:

$$\Sigma I_{TARGT}(\lambda,t_1,x,y)=\Sigma F_1(\lambda,t_1,x,y)E_1(\lambda,t_1,x,y)S_1(\lambda,t_1,x,y)R(\lambda,t_1,x,y);$$

$$\Sigma I_{cal}(\lambda,t_2,x,y)=\Sigma F_2(\lambda,t_2,x,y)E_2(\lambda,t_2,x,y)S_2(\lambda,t_2,x,y)R(\lambda,t_2,x,y);$$

where $I_{cal}$ is the measured reflectance spectrum of the calibration surface (which may comprise a white-coated electro-mechanical shutter for example), R and L are respectively the real reflectance spectra of the target and calibration surface, the subscript 1 refers to properties of the target and the calibration surface at a first time, and the subscript 2 refers to properties of the target and the calibration surface at a second, later time. The difference between $t_1$ and $t_2$ (i.e. the length of time between sequential flashes of illuminating light) may be one the order of seconds or milliseconds, for example.

For simultaneous (or sequential) imaging of the target surface and the calibration surface at the same location as the target, the model becomes:

$$F_1(\lambda,t_1,x,y)=F_2(\lambda,t_2,x,y)=F_i(\lambda);$$

$$E_i(\lambda,t_i,x,y)=E_2(\lambda,t_2,x,y)=E_i(\lambda);$$

$$S_1(\lambda,t_1,x,y)=S_2(\lambda,t_2,x,y)=S_i(\lambda);$$

$$R(\lambda)=[\Sigma I_{TARGT}/\Sigma I_{cal}]L(\lambda).$$

To measure the true target reflectance (or true color image of the target), the reflectance $L(\lambda)$ of the calibration surface should have a known spectral response within the measured wavelength range. Additionally, measurement of the target and the calibration surface should be done under similar illumination and viewing conditions. It is convenient but not mandatory for the known spectral response of the calibration surface to be flat over the measured wavelength range.

Some embodiments of the invention integrate a calibration module within a digital camera system. Such a built-in calibration module may estimate the effective spectral sensitivities of the detectors in the camera at the place and time that the camera is used to image a target.

In some embodiments, a calibration module uses images of a calibration surface coated with a standard flat response diffuse reflectance coating such as SpectraReflect™ diffuse reflectance coating (which is a water-based barium sulfate coating).

In some embodiments a calibration surface having a known reflectance at different wavelengths is provided on an inside face of a shutter covering the lens of a digital camera. The spectral response of the shutter may be established by coating the inner surface of the shutter with a standard reflectance coating so that the real spectral response $L(\lambda)$ is a known, preferably flat, spectral response (that is, $L(\lambda)$ is preferably relatively constant over the desired wavelength range).

To correct for variations with wavelength in a spectral response of a calibration surface (e.g. a coated shutter) the calibration module can use a mapping table which indicates a difference between $L(\lambda)$ and the reflectance of a diffuse reflectance standard at different wavelengths. The difference corresponds to an input value in a lookup table ("LUT"). The LUT based algorithm then corrects the measured spectral response of the calibration surface, by transforming the input value into an output value.

Some embodiments automatically set a camera to acquire images of an object illuminated with light of one or more wavelengths and images of a calibration surface illuminated in the same manner. For example, the camera may automatically acquire images of an object and images of a calibration surface (e.g. the inside of a shutter) in alternation. The shutter may be automatically opened and closed to facilitate such a sequence of images. Other possibilities include:

acquiring images of an object between two images of a calibration surface (each of these images may be acquired under the same illumination conditions); or acquiring images of an calibration surface between two images of an object (each of these images may be acquired under the same illumination conditions); or acquiring a sequence of images of a calibration surface and an object with the images of the calibration surface acquired within a short time interval of the images of the object (collectively the sequence may include one or more images of the object acquired under each of a plurality of illumination conditions and one or more images of the calibration surface acquired under each of the same plurality of illumination conditions).

Synchronizing shutter reflectance images with the acquired spectral images of the target may provide a feedback control to ensure that the digital camera system is spectrally calibrated during measurement.

For an RGB color digital camera, an illuminator may be controlled to perform simultaneous double or triple band illumination to speed up spectral image acquisition and measurements. Each triple band illumination may include light of three wavelength bands with each of the wavelength bands detectable by one of the RGB sensors of the digital camera.

With these principles in mind, some non-limiting example embodiments of the invention will now be described.

Figure 1A:
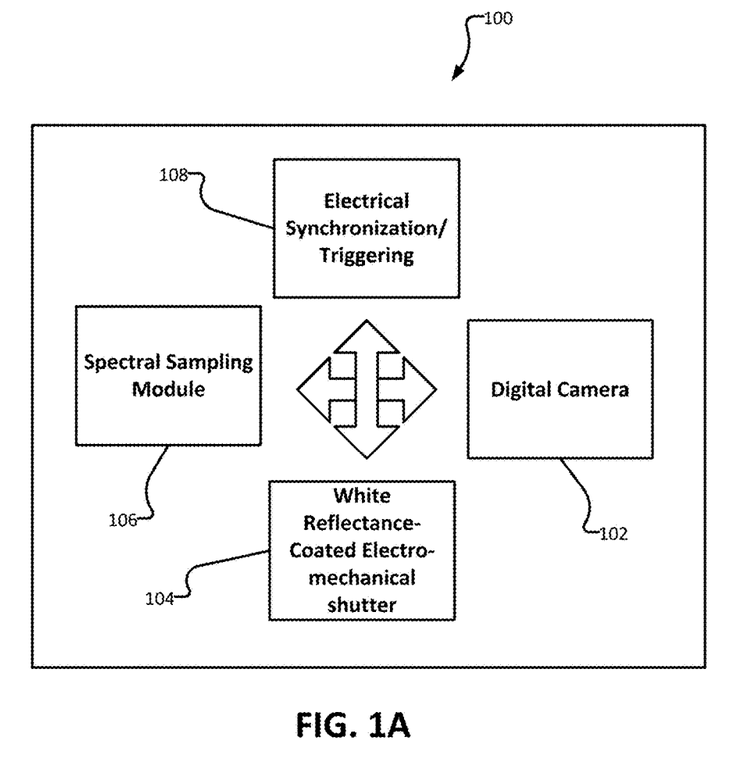
FIG. 1A is a schematic block diagram of an example apparatus for estimating reflectance image spectra using a multi-spectral imaging system with an embedded (built-in) white reflectance-coated shutter calibration module.
Figure 1B:
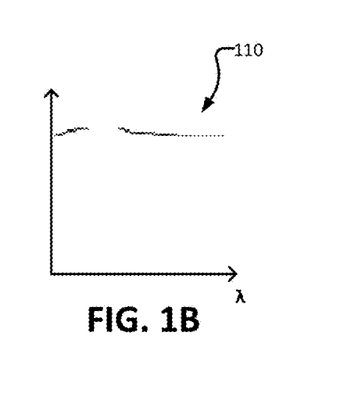
FIG. 1B shows an example reflectance spectrum for the FIG. 1A white reflectance-coated shutter calibration module.

FIG. 1A illustrates a multi-spectral imaging system 100 with an embedded (built-in) reflectance-coated shutter calibration module. System 100 includes an electro-mechanical shutter 104 coated with a material that provides a known, preferably reasonably high reflectivity. For example, the inner surface of the shutter may be white or gray. The shutter is embedded (built-in) within the housing of multi-spectral imaging system 100 together with a spectral sampling module comprising imaging lens 106; and a control module 108 to synchronize electrical triggering of the light source with opening or closing of shutter 104. Electro-mechanical shutter 104 has a known spectral response, such as the spectrum 110 shown in FIG. 1B.

In operation, system 100 sends a trigger signal from the control module 108 to close electro-mechanical shutter 104. System 100 sends another trigger signal from the control module 108 to spectral sampling module 106 to illuminate the closed shutter 104 with spectral light. System 100 then produces a series of multi-spectral images Is(λ,x,y,t) of the closed shutter 104. System 100 then sends a trigger signal from the control module 108 to open the white or grey coated electro-mechanical shutter 104. When the white or grey coated electro-mechanical shutter 104 is open, system 100 produces multi-spectral images It(λ,x,y,t) of a target object. System 100 may then process the acquired images to estimate the spectral reflectance of the surface of the target object using the following equation: Rt(λ,x,y,t)=It(λ,x,y,t)/Is(λ,x,y,t). This estimation may be performed on a pixel-by-pixel basis.

System 100 may be configured to acquire a series of multi-spectral images It(λ,x,y,t) of the surface of a target object and a series of multi-spectral images Is(λ,x,y,t) of the inner surface of electro-mechanical shutter 104 within a short time frame. In each image, the surface of a target object and the shutter 104 may be illuminated by light of a different wavelength (or different combination of discrete wavelengths). These images may then be processed on a per-pixel basis, to determine a spectral calibration which relates a detected light intensity to a reflectance of a target object at a given wavelength, using the following equation: Rt(λ,x,y,t)=It(λ,x,y,t)/Is(λ,x,y,t).

System 100 may be provided as an attachment to any standard digital camera 102, such as a smartphone camera.

Synchronization between operation of the camera to acquire images, operation of the light source of spectral sampling module 106 and operation of shutter 104 may be facilitated by software running on the camera or on a computer that controls the camera. For example, where the camera is the camera of a smartphone the software may comprise an app running on the smartphone or may be built into an operating system of the smart phone. where the camera is a stand-alone digital camera the software may be included in firmware of the digital camera, where the camera is an accessory connected to a computer the software may comprise application software executing on the computer. The software may communicate to control module 108 by a wired interface (e.g. by sending signals to control module 108 by way of a USB interface or other digital data interface provided as part of the camera or a computer controlling the camera) or by way of a wireless interface (e,g, by way of a Bluetooth™ or WiFi or other wireless signal transmitted from a wireless interface of the camera or a computer controlling the camera and received by a wireless interface connected to control module 108.

In a non-limiting example embodiment, the software executing on the camera or associated computer controls the camera to take a series of images (either as still images or a series of frames of a video image). For each image the software sends a synchronization signal to control module 108. Control module 108 controls light source of spectral sampling module 106 to emit light of one or more colors desired for the current image and controls shutter 104 to be open or closed depending on whether the current image is intended to be a calibration image or an image of the object.

Control of which images are to be calibration images and what colors of light illuminate each image may be in control module 108 or in the software that controls the camera. Where control over these parameters are in the software that controls the camera then the software may include information specifying whether shutter 104 should be open or closed and what spectral bands should be enabled for illumination either as part of the synchronization signals or in a separate communication.

The software may automatically associate together the acquired images. The software may optionally perform analysis of the acquired images.

Figure 2A:
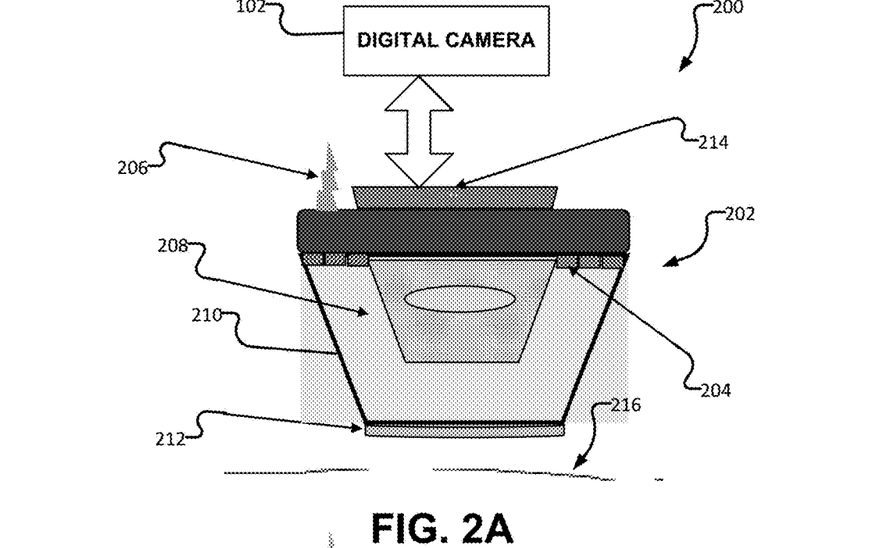
FIGS. 2A and 2B are schematic cross section views of example spectral imaging attachment devices. The device of FIG. 2A is adapted for macro-imaging. The device of FIG. 2B is adapted for distance imaging.
Figure 2B:
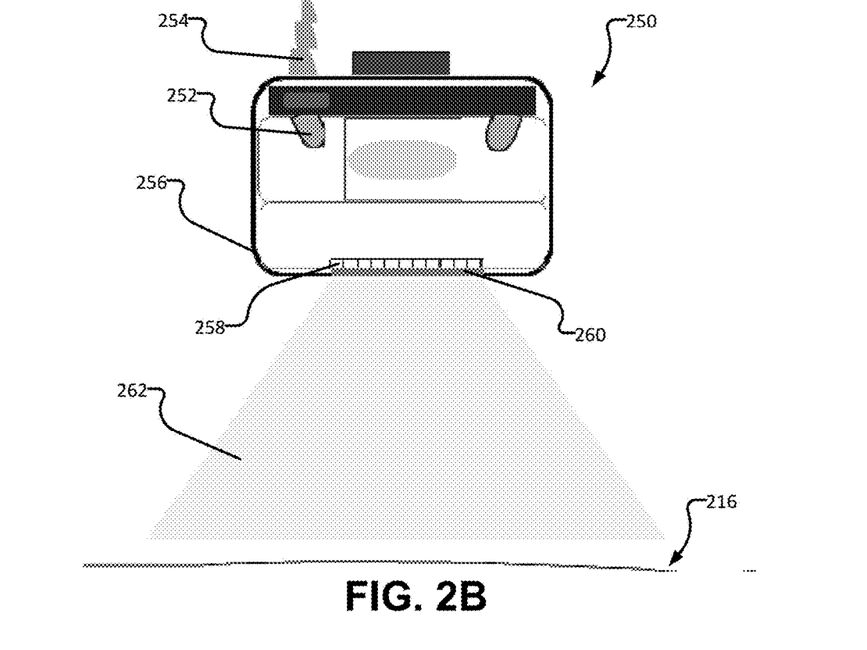

FIGS. 2A and 2B illustrate multi-spectral imaging attachments for a smartphone camera. FIG. 2A shows an attachment useful for macro imaging, such as dermoscopy imaging in the field of dermatology. FIG. 2B shows an attachment useful for distance imaging, such as clinical imaging in the field of dermatology.

As shown in FIG. 2A, apparatus 200 includes a device housing 202 that contains: a light source 204 comprising one or more monochromatic light sources for supplying spectral light illumination; an optical lens system 208 for controlling the field of view of digital camera 102 and for capturing reflected spectral light; and an electrically-controlled mechanical shutter or plate 212 coated with standard white reflectance for calibrating the spectral response of digital camera 102. Apparatus 200 further includes an electronic interface module 206 that selects the monochromatic light source(s) of light source 204 to be triggered and synchronizes the triggering sequence with the frames acquired by the attached digital camera 102. The synchronization may be achieved through an electrical communication protocol. For example, the acquisition time of image frames by the camera may be synchronized with the times that spectral light source 204 is on.

A communication protocol may initiate the on signal for spectral light source 204 when the attached digital camera 102 receives a trigger signal to acquire images. Another communication protocol may synchronize the frequency of the on time for spectral light with the frame rate of the attached digital camera 102. Apparatus 200 further includes a hood 210 to collect and diffuse light. In addition, hood 210 is useful as a fixed spacer between a target 216 (e.g. skin) and optical lens system 208 to facilitate focusing light to the target 216 for macro-imaging.

Light source 204 provides light in the visible or in the visible and near-infrared region, and may be a single unit or a combination of light sources. Light source 204 comprises an array of LEDs which emit light at different wavelengths. In order to construct a full spectral reflectance image of target 216, the number of different wavelengths may be more than ten. In some embodiments, light source 204 comprises ten or more groups of LEDs or other substantially monochrome light sources. Each group of LEDs emits light of a particular wavelength. Each group of LEDs comprises one or more LEDs. The LEDs may be arranged in two or more concentric circles. An angular optical diffuser may be used to direct light from light source 204 to evenly illuminate target 216.

Other possible light sources include: one or more lasers (e.g. one or more laser diodes (LDs)) or a broadband light source used in conjunction with narrow-band filters. The broadband light source may comprise, for example, a xenon lamp, a mercury lamp, a tungsten halogen lamp, or a metal halide lamp. The narrow-band filters may be attached to filter wheels. Light emitted from light source 204 can be modulated into a plurality of illuminating segments.

Electronic interface module 206 triggers illumination by light source 204 such that target 216 is illuminated by light of one or more selected wavelengths in a manner that is synchronized with acquisition of image frames captured by attached digital camera 102. The digital camera 102 may be operating in a video acquisition mode or a still-image acquisition mode. The captured image frames coming from digital camera 102 and synchronized with the illumination sequence of light source 204 are collected and analyzed by a processing unit (not shown) to estimate the reflectance spectrum of target 216. Processing may occur automatically upon acquisition of the images or may be performed subsequently.

A processing unit receives multi-spectral images of a target 216, captured at different wavelengths. By correlating the On/Off timing of spectral light with the frame acquisition time, the processing unit (not shown) marks each image with its corresponding wavelength(s) of illumination. For example, the processing unit (not shown) receives multi-spectral images of the target 216 It1(x,y, λ1), It2(x,y, λ2), It3(x,y, λ3), . . . Itn(x,y, λn) and multi-spectral images of the coated shutter 212 Is1(x,y,λ1), Is2(x,y, λ2), Is3(x,y, λ3), . . . Isn(x,y, λn) in real time. To estimate the spectral reflectance images R(x, y, λ) of the target 216, the processing unit normalizes the multi-spectral images of the target 216 with the multi-spectral images of the coated shutter 212.

The processing unit may use the estimated spectral reflectance images to estimate perceptual color components, e.g. the RGB values. This relies on the CIE XYZ color space model: a $$X = d\lambda \Sigma x(\lambda) I(\lambda)$$

$$Y = d\lambda \Sigma y(\lambda) I(\lambda)$$

$$Z = d\lambda \Sigma z(\lambda) I(\lambda)$$

Where x (λ), y (λ), and z (λ) are the CIE color matching functions, and I (λ) is the target reflectance spectra.

The processing unit may be embedded in camera 102 or housing 202, or may be external. In some embodiments, processing is performed in all or in part by a smartphone app (or a web app) that runs on the device hosting camera 102 instead of by a separate processing unit.

Optical lens system 208 may comprise macro lenses with variable optical fields of view. The macro lenses may be corrected by suitable coatings for use in the spectral range of 400 nm-800 nm. Diffuse white reflectance material is coated or mounted on the side of shutter 212 which is facing lens system 208 Apparatus 200 uses the spectral measurements obtained from shutter 212 to calibrate the spectral response of the color sensor in digital camera 102.

FIG. 2B shows an example embodiment of the multi-spectral imaging device with an attachment for use with distance imaging (together apparatus 250). Apparatus 250 includes a diffuser 258 to diffuse light to illuminate larger areas. Apparatus 250 may be used at a distance and not in direct contact with the target 216. Diffuse reflection is calibrated using near light measurements 258 and then diffused 260 for wide-field illumination. The distance imaging device may then function in the same manner as apparatus 200 as described above.

Figure 3A:
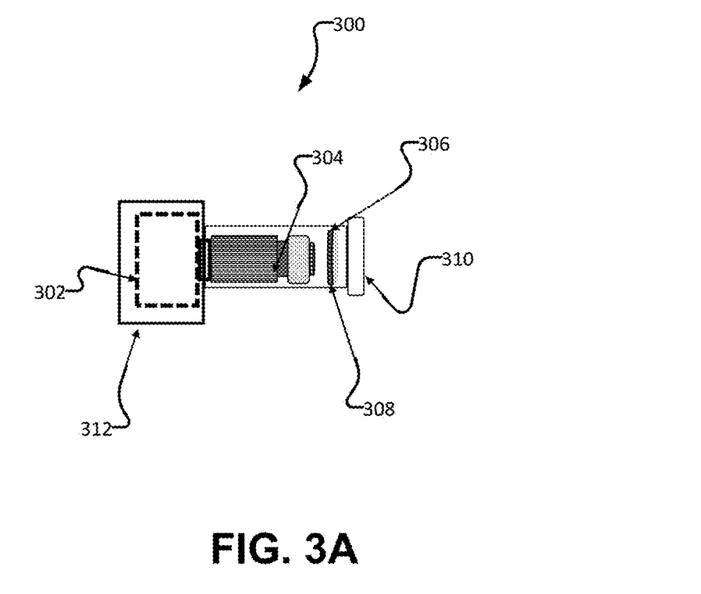
FIGS. 3A and 3B are schematic views of a multi-spectral imaging camera with a built-in white reflectance-coated shutter calibration module.

FIG. 3A shows a multi-spectral imaging digital camera system 300 with built-in spectral calibration, according to another example embodiment of the invention. System 300 comprises a camera sensor 302 housed in a camera enclosure 312, a lens 304 (typically a macro lens), an LED ring 308 comprising emitters of different monochromatic wavelengths (e.g. wavelengths in the range of 400 nm-1000 nm) and coupled to a polarizer 306, and an electrically-controlled shutter 310 (such as rotary drive shutter) coated with standard white reflectance. Digital camera system 300 may operate to acquire multi-spectral images as described above.

Figure 3B:
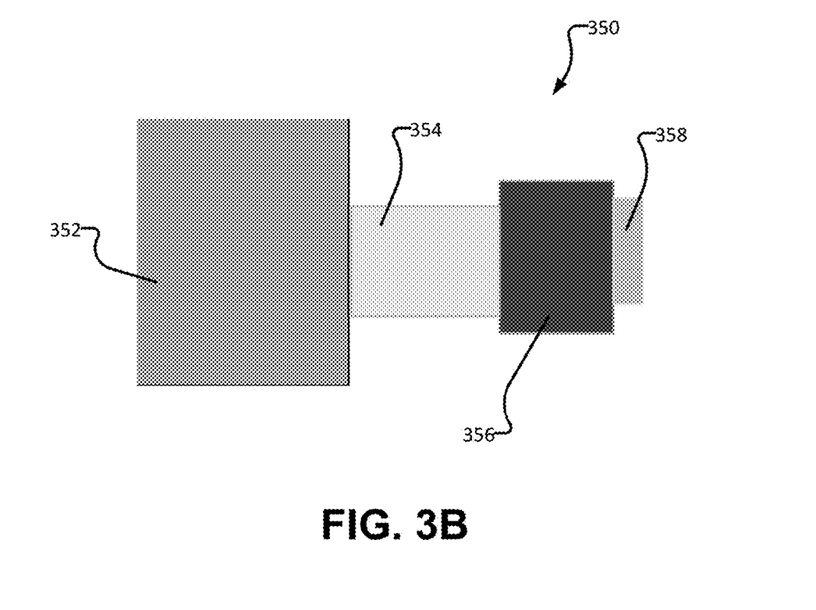

FIG. 3B shows an example absorption filter-based spectral imaging digital camera system with a built-in spectral calibration module, together apparatus 350. For example, the digital camera system may comprise tunable filters or acousto-optic filters 356. Possible embodiments of light source for apparatus 350 include a xenon lamp, a mercury lamp, a tungsten halogen lamp, a metal halide lamp, a laser, one or more laser diodes (LDs), and/or natural light. Apparatus 350 includes an electrically-controlled shutter 358. The shutter 358 has an opening to allow light to illuminate the shutter 358. Light reflected from the shutter 358 is filtered through tunable filters or acousto-optic filters 356 to produce light of discrete wavelengths. The filtered light is then used to estimate the spectral reflectance images R(x, y, λ) of a target.

Figure 4A:
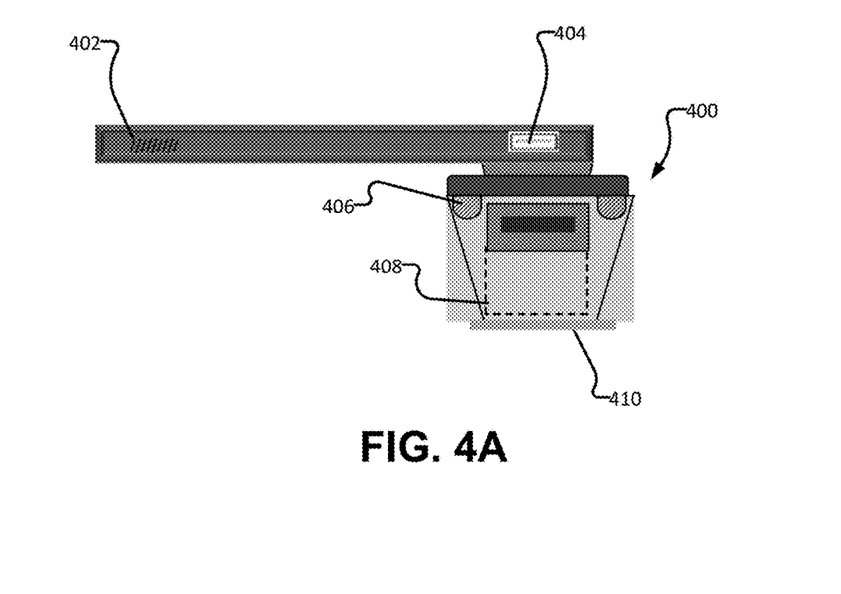
FIGS. 4A and 4B respectively illustrate example spectral imaging attachments for a smartphone and a webcam or digital camera.

FIG. 4A shows a smartphone attachment 400, according to another example embodiment of the invention. Multi-spectral imaging attachment 400 may be connected to a smartphone 402. A smartphone app may be used to synchronize the illumination sequence of a spectral light source with the acquired image frames of a target from the smartphone camera 404. In operation, to obtain spectral reflectance measurements using the integrated device and smartphone camera 404, an initial measurement is obtained with a white or grey reflectance shutter 410 covering the field of view of camera 404. A smartphone app sends a trigger signal to close the shutter 410. The smartphone app then sends a trigger signal to turn on spectral light of a specified wavelength. The smartphone app then sends a trigger signal to the smartphone camera to acquire an image of the shutter 410 in real time. Once an image is acquired, the smartphone app sends a trigger signal to turn off spectral light of a the specified wavelength and to turn on spectral light of a different wavelength. This process repeats until spectral light of all different wavelengths have been used to produce multi-spectral images of the coated shutter 410: Is1(x,y,λ1), Is2(x,y, λ2), Is3(x,y, λ3), . . . Isn(x,y, λn) in real time. The smart app then sends a trigger signal to open the coated shutter 410. With the shutter 410 removed from the field of view of camera 404, multi-spectral images of a target may be acquired: It1(x,y, λ1), It2(x,y, λ2), It3(x,y, λ3), . . . Itn(x,y, λn). The smartphone app may synchronize the frequency of the on time for spectral light with the frame rate of the attached digital camera. The acquired multi-spectral images may be stored in a data store of the smartphone 402 and/or transmitted to another destination (e.g. the acquired images may be uploaded to a FTP site or to a cloud-based data store or transmitted to an email account or the like.

An algorithm, which may be implemented by an app stored on smartphone 402 or by a processor on a separate device may be used to determine the reflectance spectra of the imaged target on a pre-pixel basis, based on the calibration surface (e.g. shutter 410) and target surface measurements. To estimate the spectral reflectance images R(x, y, λ) of the target, the algorithm normalizes the multi-spectral images of the target with the multi-spectral images of the coated shutter 410.

Figure 4B:
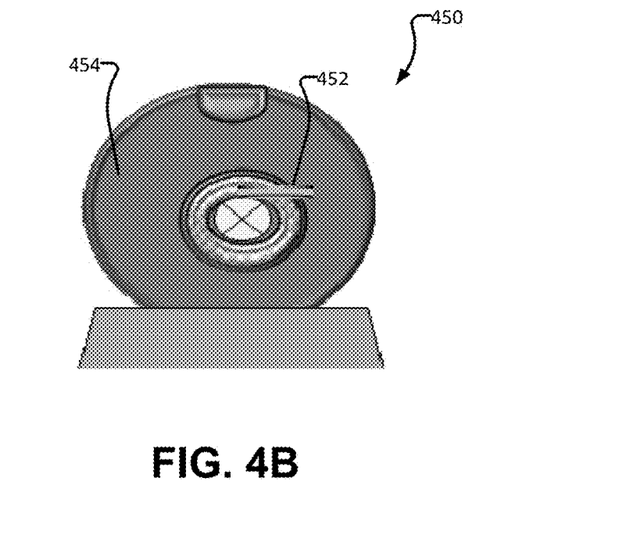

In another example embodiment, an attachment 452 can be used with a web cam 454, as shown in FIG. 4B. A computer program may be used to synchronize the illumination sequence of a spectral light source with the acquired image frames of a target from webcam 454.

Figure 5:
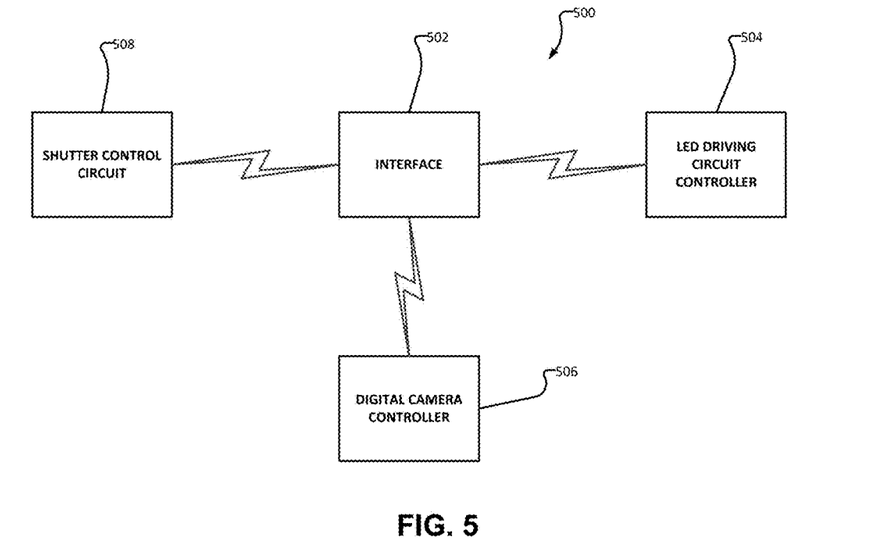
FIG. 5 is a block diagram illustrating a system for electronic synchronization between an electro-optical attachment and a smartphone/digital camera processor.

FIG. 5 is a block diagram 500 showing selected electrical components in a multi-spectral imaging attachment for use with a smartphone camera, which may be used to generate synchronized video frames for different illumination wavelengths. This embodiment includes an interface portion 502 which receives frame timing signals from the camera. The timing signals may be electrical signals, such as TTL signals and pulsed electrical signals. Interface portion 502 may also interact with a digital camera controller 506 and a shutter control circuit 508 in order to facilitate illumination of the selected LEDs. Interface portion 502 triggers an LED driving circuit 504 to control illumination of selected LEDs in a synchronized manner. The synchronization can be wireless, preferably using Bluetooth™, or can be implemented through a wired connection. For example, interface portion 502 sends concurrent electrical signals to the camera 506 to start frame acquisition; to the shutter 508 to close the shutter; and to LED driving circuit 504 to start illumination by LEDs of a specified wavelength. When interface portion 502 receives a trigger signal from the camera 506 indicating that multi-spectral images have been acquired from light of a specified wavelength, interface portion 502 sends a trigger signal to stop illumination by light of a specified wavelength but start illumination by light of a different wavelength. This process repeats until spectral light of all different wavelengths have been used to produce multi-spectral images.

For a typical RGB color camera, illumination can be triggered at three different wavelengths simultaneously, with one wavelength in the blue band of the spectrum, a second wavelength in the green band of the spectrum, and a third wavelength in the red band of the spectrum.

Figure 6A:
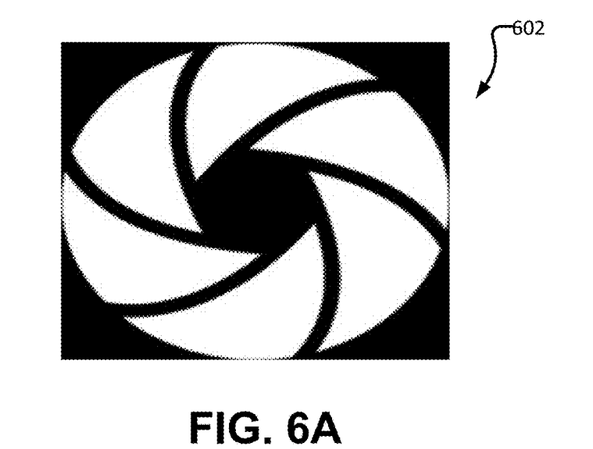
FIGS. 6A, 6B, and 6C illustrate example shutter types suitable for white reflectance-coating.
Figure 6B:
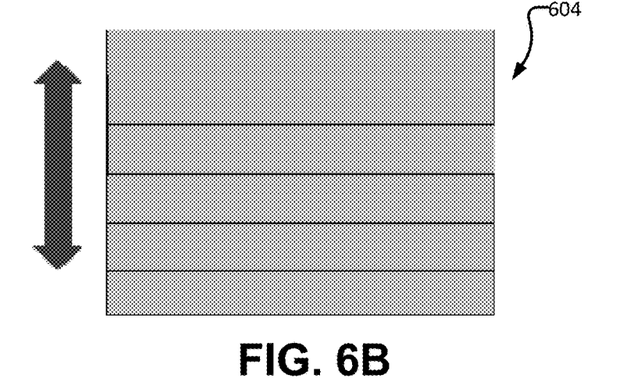
Figure 6C:
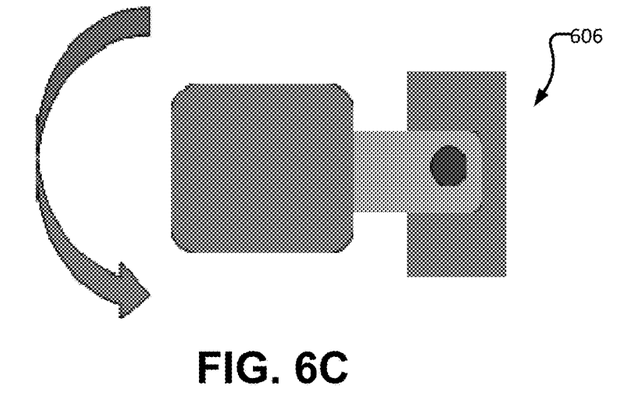

FIG. 6 shows some examples of electro-mechanical shutter mechanisms 602, 604, and 606, which are suitable for use with a built-in spectral calibration module. Shutter 602 is a leaf shutter comprising overlapping metal blades. When the shutter control circuit receives a trigger signal, shutter 602 opens by moving the blades to uncover the lens. Shutter 604 is a focal plane shutter. The two curtains of shutter 604 move in opposite directions to uncover the lens. Shutter 606 is a flag shutter. The blade of shutter 606 pivots downward to uncover the lens. Other possible electro-mechanical shutter mechanisms include rotor drive shutters solenoid shutters, and stepper motor shutters.

Apparatus as described herein may be used to acquire digital images for skin diagnosis and computer-aided diagnosis (CAD), for follow-ups using image archiving, and for tele-dermatology, among other applications.

Figure 7:
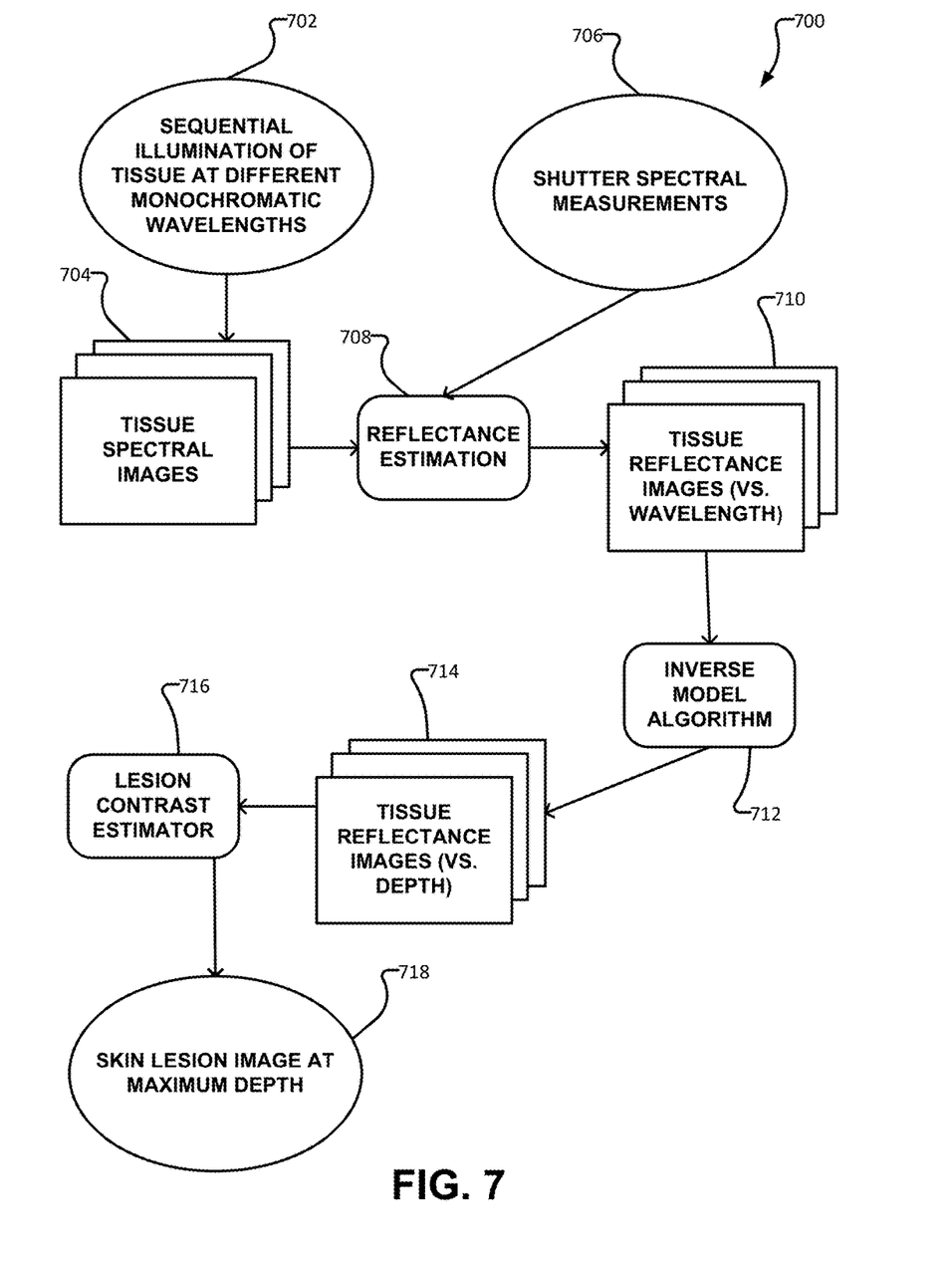
FIG. 7 is a process flow diagram illustrating the operation of a mobile app or algorithm for quantifying the depth of skin lesions.

FIG. 7 is a block diagram of an example method 700 for generating depth-resolved skin images from acquired spectral images. Method 700 accesses optical properties of the tissue being imaged. The optical properties of the tissue relate to the penetration depth of light of different wavelengths. These properties may include optical absorption coefficient and optical scattering coefficient. For example, skin and the coated shutter may be imaged while being illuminated with light of multiple different wavelengths to produce a set of multi-spectral images. The images may then be used to measure the reflectance spectra of skin as a function of wavelength. An inverse model algorithm using a radiative transfer model is used to calculate an expected depth of penetration at each of the plurality of wavelengths, while taking into account the optical properties of the tissue being imaged.

In an example embodiment apparatus as described above is used to image a skin lesion. The apparatus yields images of the skin lesion illuminated by light of a plurality of corresponding wavelengths. A computer implemented algorithm is used to calculate the contrast of the skin lesion to the surrounding tissue. The algorithm transforms the contrast images at different wavelengths into contrast images at different depths. As such, the algorithm creates 2D cross sectional images of skin lesion at different depths, which allow the user to visualize the skin lesion.

Method 700 will now be described in detail. Method 700 may be implemented, for example, using apparatus 200 as shown in FIG. 2A. In block 702, light source 204 (e.g. a plurality of LEDs) sequentially illuminates target 216 with different monochromatic wavelengths (for example, in total ten or more wavelengths in the range of 400 nm-1000 nm). This produces a plurality of spectral images 704 of target 216. Spectral measurements 706 of shutter 212 may be combined with spectral images 704 to create a reflectance estimate 708 of target 216. This results in a plurality of reflectance images 710 of target 216 indexed by the wavelength of the illumination.

Reflectance images 710 are then provided to inverse model algorithm 712. Algorithm 712 may use a radiative transfer model, such as a diffusion approximation model, to calculate the expected depth of penetration at each wavelength of illumination, taking into account the optical properties of target 216 as measured in block 702. Algorithm 712 outputs a plurality of reflectance images 714 of target 216 indexed by the expected depth of penetration of target 216.

Reflectance images 714 are then input into algorithm 716, which calculates the contrast of target 216 to its surroundings. For example, target 216 may be a skin lesion, and algorithm 716 may calculate the contrast in the reflectance of the skin lesion with the reflectance of tissue surrounding the lesion. Optionally, at block 718, the maximum depth of target 216 (for example, a skin lesion) may be calculated, and a corresponding depth image may be produced.

Figure 8A:
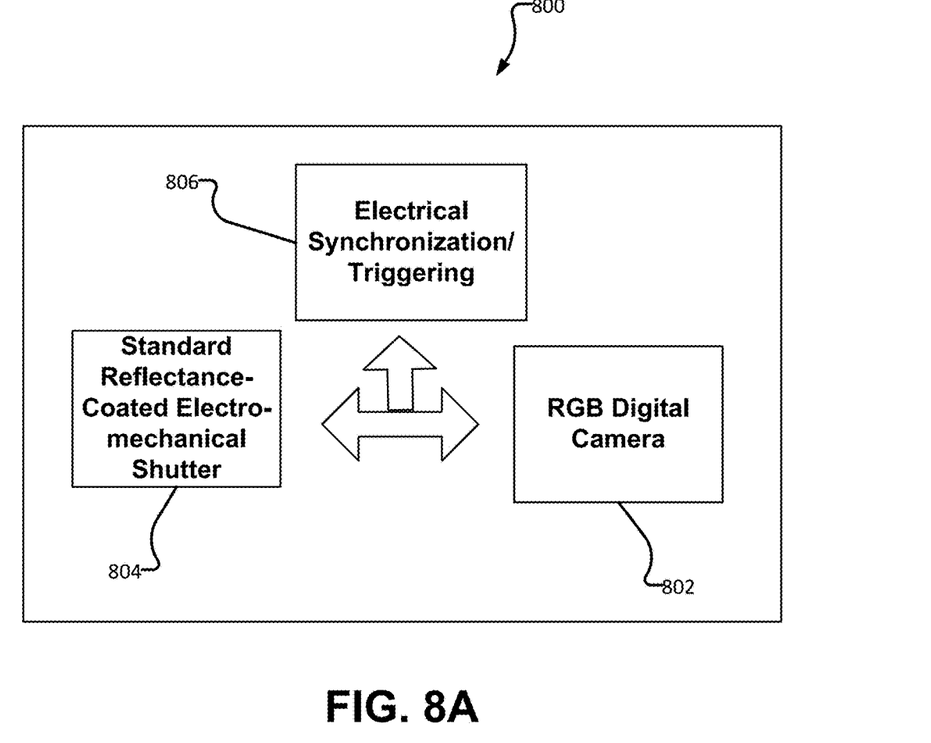
FIG. 8A is a schematic block diagram of an example RGB digital camera having an embedded standard reflectance-coated shutter calibration module.
Figure 8B:
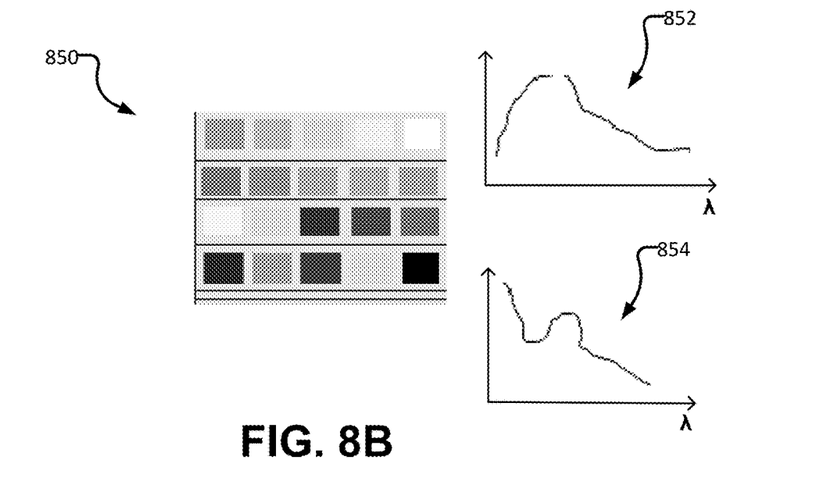
FIG. 8B is an example of the FIG. 8A standard reflectance-coated shutter calibration module, with some example possible reflectance spectra.

FIG. 8 is a schematic block diagram of an example RGB digital camera 802 having an embedded shutter calibration module. The shutter calibration module may comprise, for example, an electro-mechanical shutter 804, such as a focal plane shutter, coated with a number of different color reflectance surfaces 850 having known reflectance spectra (e.g. spectra 852 and 854), as shown in FIG. 8B.

Digital camera 802 may be used to enhance the effect of natural light and to provide an independent light source. For example, digital camera 802 may capture a plurality of RGB digital images of a target. These images may then be re-calibrated under the same viewing and illumination conditions (i.e. the same time and the same place) using shutter 804. Digital camera 802 may measure the surrounding natural light reflected from the coated shutter 804 either before or during the image acquisition of a target. Digital camera 802 may be configured to use measurements of the coated shutter 804 to calibrate the spectral reflectance matrix of the target. This process produces a more accurate spectral reflectance matrix $(H_t)$. $H_t$ may then be used to calibrate the acquired spectral images to estimate the spectral reflectance of the target.

$$\stackrel{H_t}{\longleftrightarrow}$$

$$\begin{bmatrix} \lambda 1 \\ \lambda 2 \\ \lambda 3 \\ \lambda 4 \\ \lambda k \end{bmatrix} = \begin{bmatrix} h1R & h1G & h1B \\ h2R & h2G & h2B \\ h3R & h3G & h3B \\ & h4 & \\ & h5 & \\ & hk & \end{bmatrix} \cdot \begin{bmatrix} R \\ G \\ B \end{bmatrix}$$

A spectral reflectance matrix Λ may be obtained from the calibration procedure described above. To estimate the spectral reflectance matrix Λ, a regression analysis, such as the Wiener estimation, may be use to analyze the RGB measurements obtained from a number of different color reflectance surfaces 850 having known reflectance spectra. The spectral reflectance matrix Λ may be used to estimate spectral reflectance of other targets, assuming the images of these targets have been acquired under the same illumination and viewing conditions.

The measurements of coated shutter 804 may be used as reference measurements.

Digital camera 802 may capture a plurality of RGB digital images of target 216. These images may then be re-calibrated under the same viewing and illumination conditions (i.e. the same time and the same place) using shutter 804 and a dynamic calibration algorithm.

A dynamic calibration algorithm for updating the reflectance spectrum matrix, using the coated shutter reflectance measurement, is proposed to produce updated estimation matrix.

Figure 9:
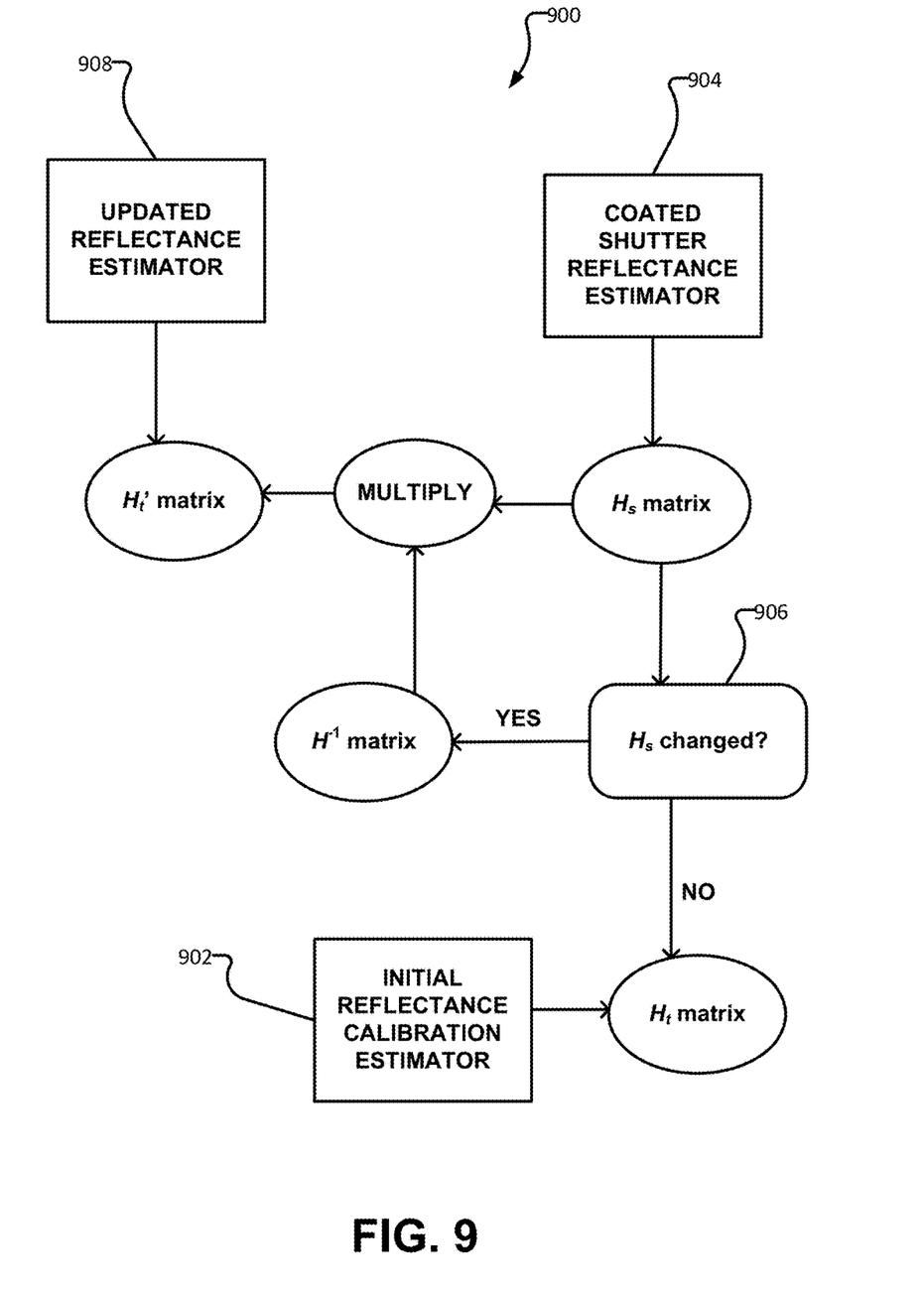
FIG. 9 is a process flow diagram illustrating a dynamic spectral calibration algorithm.

FIG. 9 is a block diagram of an example dynamic calibration algorithm 900. In block 902, the initial calibration of RGB digital camera 802 is performed using a color standard placed at target 216 to obtain the target RGB reflectance estimator matrix $H_t$. In block 904, shutter calibration may then be performed to obtain the coated shutter RGB reflectance estimator matrix $H_s$, as well as the correlation between $H_t$ and $H_s$. The system calibration matrix $H=H_t/H_s$ should be fixed for a particular RGB digital camera 802. For new measurements under different viewing and illumination conditions, the reflectance of shutter 804 may be evaluated dynamically. If the reflectance of shutter 804 is changed in response to new viewing or illumination conditions, then $H_s$ is updated (as in block 906) and used to calculate an updated target RGB reflectance estimator matrix $H_t'=H_s \cdot H^{-1}$ (block 908).

In this way, RGB images obtained under different viewing and/or illumination conditions may be re-calibrated under the same viewing and illumination conditions as the initial calibration conditions. For example, when the built-in calibration device detects a change in viewing and/or illumination conditions, it may dynamically re-calibrate the camera system by updating H based on current viewing and illumination conditions.

Figure 10A:
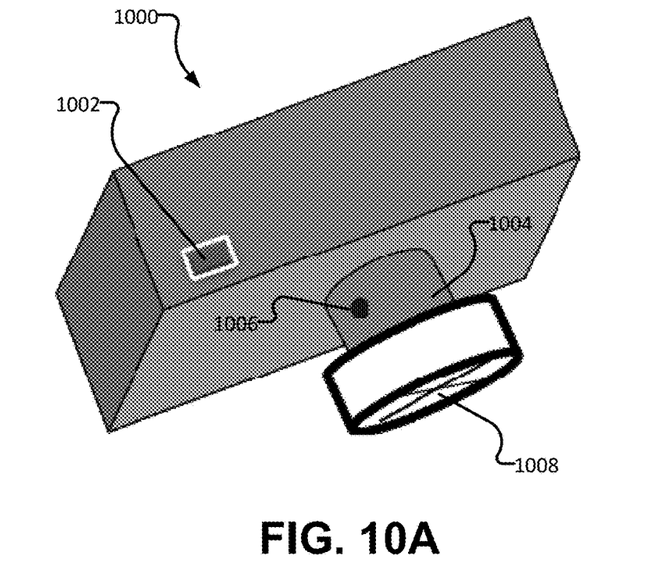
FIGS. 10A and 10B are schematic illustrations of an example digital camera having an embedded standard reflectance-coated shutter calibration module.
Figure 10B:
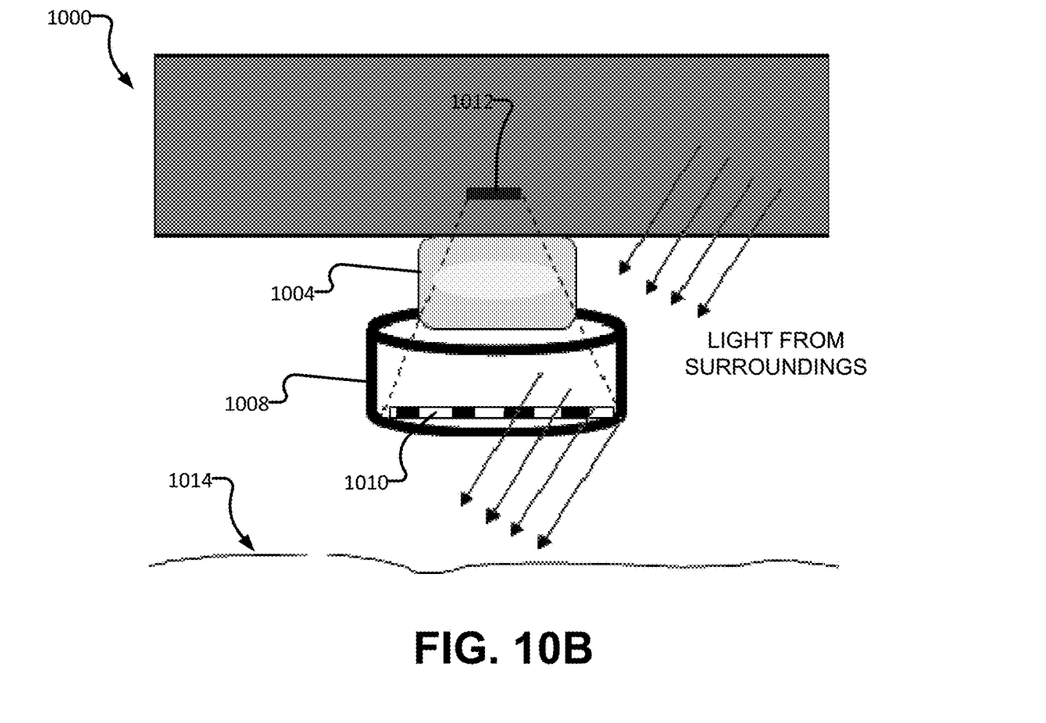

FIGS. 10A and 10B are schematic illustrations of an example digital camera 1000 having an embedded standard reflectance-coated shutter calibration module and equipped to implement dynamic calibration (e.g. using method 900), according to an example embodiment of the invention. FIG. 10A shows camera 1000 with built-in coated shutter calibration module 1008. This system may be used to estimate the reflectance spectra of a target 1014, as shown in FIG. 10B. Camera 1000 supports a camera lens 1002 (preferably an autofocus lens, variable lens, or other lens with a large depth of field), which is connected to module 1008.

Module 1008 may be made of transparent plastic or glass so that incident light from the surroundings is able to illuminate shutter surface 1010. This allows the surroundings to be sampled and measured during shutter image acquisition. The camera system is able to trigger the shutter to open and close, and is able to synchronize shutter calibration with the acquisition of digital camera frames. Dynamic re-calibration of module 1008 may remove the confounding effect of illuminant color, such that camera 1000 only acquires surface color images (i.e. RGB bands measured for a surface viewed under canonical lighting conditions).

While preferred embodiments of present invention are shown and described above, it is envisioned that those skilled in the art may devise various modifications of the present invention without departing from the spirit and scope presented herein.

Interpretation of Terms

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

While elements are at times shown as being performed sequentially, they may instead be performed simultaneously or in different sequences. It is therefore intended that the following claims are interpreted to include all such variations as are within their intended scope.

Where a component (e.g. a camera, sensor, shutter, control, software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

What is claimed is:

1. A spectral light apparatus that when integrated to a digital camera (such as smartphone camera) produces spectral reflectance and color value measurements of an object/scene recorded by the digital camera, the apparatus comprising a housing supporting:
    a. a spectral light source operable to selectively produce a spectral flash light sequence comprising a sequence of narrow-band light to illuminate a target;
    b. an optical lens system comprising at least one lens arranged to align a field of view of the digital camera to an enclosure opening comprising a distal end which defines a spectral image field of view;
    c. an electro-mechanical shutter or plate covering the spectral image field of view when closed, the shutter or plate having an inner surface having a known reflectance spectrum; and d. a control module operable to synchronize electrical triggering of the spectral flash light sequence with a sequence of open and shut states of the shutter or plate with a sequence of image acquisitions by the camera.

2. The apparatus according to claim 1 comprising processing software configured to execute on a processor of the apparatus to acquire a spectral reflectance image of an object by processing images captured by the digital camera.

3. The apparatus according to claim 2 wherein the software is configured to calculate the spectral reflectance of the object using the captured images, wherein the images processed include images of the object and images of the electro-mechanical shutter or plate.

4. The apparatus according to claim 1 wherein the shutter or plate comprises a white or grey reflectance surface.

5. The apparatus according to claim 1 wherein the shutter or plate is movable between a closed configuration in which the shutter or plate shields the field of view of the digital camera and an open configuration in which the shutter or plate clears the field of view of the digital camera.

6. The apparatus according to claim 1 wherein the control module interfaces wirelessly and/or through wire connection with circuitry of a smartphone.

7. The apparatus according to claim 6 wherein LEDs or laser diodes are mounted in a circular or rectangular array central around an optical axis of the digital camera.

8. The apparatus according to claim 1 wherein the control module triggers a plurality of LEDs to emit light of a corresponding plurality of different wavelengths simultaneously.

9. The apparatus according to claim 8 wherein the control module triggers three of the plurality of LEDs to emit light of three corresponding different wavelengths simultaneously.

* * * * *